(12) United States Patent
Heida et al.

(10) Patent No.: US 10,968,152 B2
(45) Date of Patent: Apr. 6, 2021

(54) SIMPLIFIED PROCESS FOR ISOLATING PURE 1,3-BUTADIENE

(71) Applicant: BASF SE, Ludwigshafen am Rhein (DE)

(72) Inventors: Bernd Heida, Ellerstadt (DE); Tobias Keller, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/493,185

(22) PCT Filed: Mar. 12, 2018

(86) PCT No.: PCT/EP2018/056050
§ 371 (c)(1),
(2) Date: Sep. 11, 2019

(87) PCT Pub. No.: WO2008/166961
PCT Pub. Date: Sep. 20, 2018

(65) Prior Publication Data
US 2020/0010387 A1 Jan. 9, 2020

(30) Foreign Application Priority Data
Mar. 13, 2017 (EP) .................................... 17160642

(51) Int. Cl.
*C07C 11/167* (2006.01)
*B01D 3/14* (2006.01)
(Continued)

(52) U.S. Cl.
CPC ............ *C07C 11/167* (2013.01); *B01D 3/143* (2013.01); *B01D 3/40* (2013.01); *C07C 7/08* (2013.01)

(58) Field of Classification Search
CPC ............ C07C 11/167; C07C 7/04; C07C 7/08; B01D 3/143; B01D 3/40
See application file for complete search history.

(56) References Cited

U.S. PATENT DOCUMENTS

| 4,859,286 A | 8/1989 | Kaibel et al. | |
| 2004/0045804 A1* | 3/2004 | Bohner | ...................... C07C 7/04 |
| | | | 203/1 |

(Continued)

FOREIGN PATENT DOCUMENTS

| DE | 101 05 660 A1 | 8/2002 |
| EP | 0 284 971 A2 | 10/1988 |

(Continued)

OTHER PUBLICATIONS

International Search Report dated May 29, 2018 in PCT/EP2018/056050 (with English translation), 5 pages.

(Continued)

*Primary Examiner* — Youngsul Jeong
*Assistant Examiner* — Jason Y Chong
(74) *Attorney, Agent, or Firm* — Grüneberg and Myers PLLC

(57) ABSTRACT

A process for isolating pure 1,3-butadiene from a crude $C_4$ fraction, which produces pure 1,3-butadiene having a prescribed maximum content of at least one low boiler and a prescribed maximum content of 1,2-butadiene, in each case based on 1,3-butadiene, wherein (a) a low boiler fraction and a high boiler fraction are separated off by distillation from the crude $C_4$ fraction, giving a purified $C_4$ fraction whose content of the at least one low boiler, based on 1,3-butadiene, is equal to or lower than the prescribed maximum content of the at least one low boiler and whose content of 1,2-butadiene, based on 1,3-butadiene, is equal to or lower than the prescribed maximum content of 1,2-butadiene; (b) the purified $C_4$ fraction is subjected to at least one extractive (Continued)

distillation using a selective solvent, giving at least a fraction comprising butanes and butenes and a pure 1,3-butadiene fraction, is described. The process makes a pure distillation column dispensable.

19 Claims, 1 Drawing Sheet

(51) Int. Cl.
*B01D 3/40* (2006.01)
*C07C 7/08* (2006.01)

(56) References Cited

U.S. PATENT DOCUMENTS

| | | |
|---|---|---|
| 2004/0065538 A1 | 4/2004 | Bohner et al. |
| 2006/0241329 A1 | 10/2006 | Heida |
| 2007/0039813 A1* | 2/2007 | Heida .................... C07C 7/08 203/2 |
| 2018/0361270 A1* | 12/2018 | Asprion ................. B01D 3/40 |
| 2019/0169149 A1* | 6/2019 | Teles ..................... B01D 5/006 |
| 2019/0210989 A1* | 7/2019 | Teles .................... C07D 303/04 |
| 2019/0322634 A1* | 10/2019 | Teles .................... C07D 301/32 |
| 2020/0339490 A1* | 10/2020 | Heida ................ B01D 11/0488 |

FOREIGN PATENT DOCUMENTS

| | | |
|---|---|---|
| WO | WO 2005/009931 A2 | 2/2005 |
| WO | WO 2011/110562 A1 | 9/2011 |
| WO | WO 2013/083536 A1 | 6/2013 |

OTHER PUBLICATIONS

International Preliminary Report on Patentability and Written Opinion of the International Searching Authority dated Sep. 17, 2019 in PCT/EP2018/056050 filed Mar. 12, 2018 (with English translation), 10 pages.

Gerd Kaibel, et al., "Möglichkeiten zur ProzeBintegration bei Destillativen Trennverfahren" Chem.-Ing. Techn. vol. 61, No. 2, 1989, pp. 104-112 (with English Abstract).

G. Kaibel, et al., "Thermodynamics-Guideline for the Development of Distillation Column Arrangements" Gas Separation and Purification, vol. 4, No. 2, 1990, pp. 109-114.

U.S. Appl. No. 15/741,350, dated Jan. 2, 2018, US 2018/0361270 A1, Norbert Asprion, et al.

U.S. Appl. No. 16/318,221, dated Jan. 16, 2019, US 2019/0169149 A1, Joaquim Henrique Teles, et al.

U.S. Appl. No. 16/315,345, dated Jan. 4, 2019, US 2019/0322634 A1, Joaquim Henrique Teles, et al.

U.S. Appl. No. 16/315,680, dated Jan. 7, 2019, US 2019/0210989 A1, Joaquim Henrique Teles, et al.

U.S. Appl. No. 16/475,566, dated Jul. 2, 2019, US 2020/0339490 A1, Bernd Heida, et al.

* cited by examiner

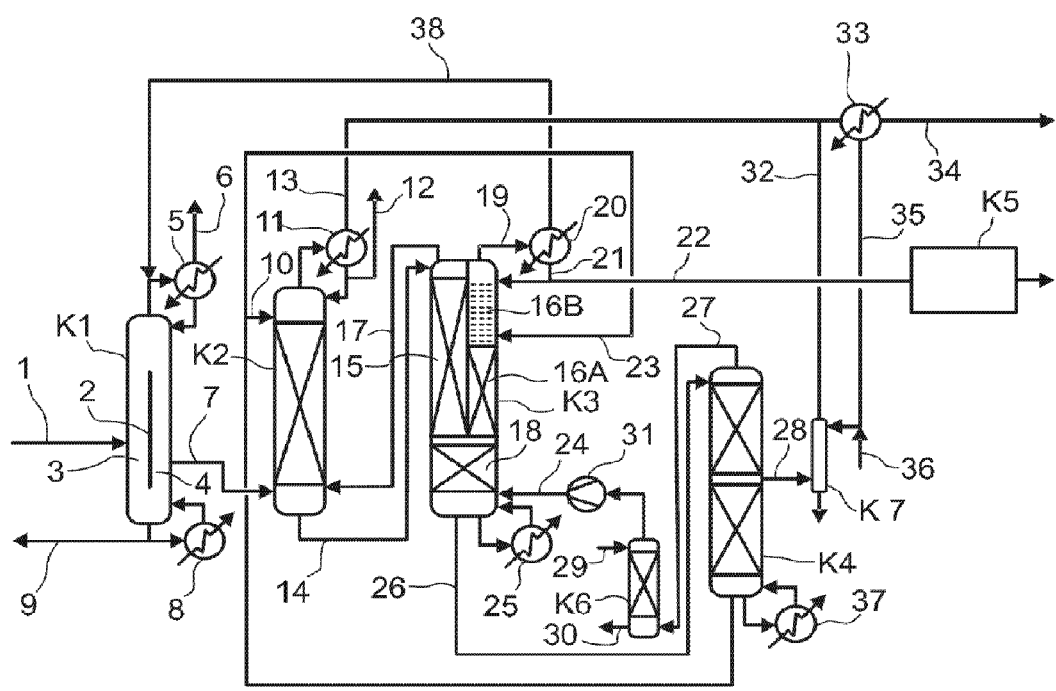

SIMPLIFIED PROCESS FOR ISOLATING PURE 1,3-BUTADIENE

The present invention relates to a process for isolating pure 1,3-butadiene from a crude $C_4$ fraction.

In industry, 1,3-butadiene is generally obtained from $C_4$ fractions, i.e. from mixtures of hydrocarbons in which $C_4$-hydrocarbons, especially 1-butene, i-butene and 1,3-butadiene, are predominant.

$C_4$ fractions are obtained, for example, in the preparation of ethylene and propylene by thermal cracking, usually in steam crackers, in particular naphtha or gas crackers. Furthermore, 1,3-butadiene-comprising $C_4$ fractions are obtained in the catalytic dehyrogeneration of n-butane and/or n-butene. Any mixture comprising n-butenes can be used as feed gas mixture for the oxidative dehydrogenation of n-butenes to 1,3-butadiene. Gas mixtures comprising n-butenes which are used as feed gas in the oxidative dehydrogenation of n-butenes to 1,3-butadiene can be prepared by nonoxidative dehydrogenation of gas mixtures comprising n-butane. The $C_4$ fractions comprising 1,3-butadiene will hereinafter be referred to as crude $C_4$ fractions. They comprise not only small amounts of $C_3$- and $C_5$-hydrocarbons but generally also acetylenes (methylacetylene, ethylacetylene and vinylacetylene).

It is known that pure 1,3-butadiene can be isolated from crude $C_4$ fractions by a sequence of particular process steps in which a crude 1,3-butadiene is firstly isolated from the crude $C_4$ fraction and the crude 1,3-butadiene is then purified further in order to isolate the pure 1,3-butadiene therefrom. Crude 1,3-butadiene is a mixture comprising from about 90 to 99.5% by weight of 1,3-butadiene, in particular from 98 to 99% by weight of 1,3-butadiene. The specifications for pure 1,3-butadiene frequently provide for a minimum content of 1,3-butadiene of 99.6% by weight and a maximum permissible content of acetylenes and of 1,2-butadiene of in each case 20 ppm, based on the mass of the pure 1,3-butadiene.

The isolation of 1,3-butadiene from $C_4$ fractions is a complex separation task because of the small differences in the relative volatilities of the components. For this reason, an extractive distillation, i.e. a distillation with addition of a selective solvent which has a boiling point higher than that of the mixture to be separated and which increases the differences in the relative volatilities of the components to be separated, is carried out. The crude 1,3-butadiene obtained in this way is, in order to meet specifications, purified by distillation to give pure 1,3-butadiene.

In all the processes for the extractive distillation of $C_4$ fractions using selective solvents, the selective solvent becomes, as a result of the $C_4$ fraction to be separated being conveyed in vapor form in countercurrent to the liquid selective solvent under suitable thermodynamic conditions, generally at low temperatures, usually in the range from 20 to 80° C., and at moderate pressures, frequently from about 3 to about 6 bar, loaded with the components of the $C_4$ fraction to which it has a greater affinity, while the components to which the selective solvent has a lower affinity remain in the vapor phase and are taken off as overhead stream. The components are subsequently fractionally liberated from the selective solvent in the loaded solvent stream under suitable thermodynamic conditions, i.e. at elevated temperature and/or relatively low pressure.

For example, according to WO 2011/110562 A1, a crude $C_4$ fraction is selectively hydrogenated, high-boiling constituents are subsequently separated off from the selectively hydrogenated $C_4$ fraction and the remaining $C_4$ fraction is then worked up further by extractive distillation in order to obtain crude 1,3-butadiene. The crude 1,3-butadiene is purified further by pure distillation to give pure 1,3-butadiene.

DE 101 05 660 discloses a process for isolating crude 1,3-butadiene from a $C_4$ fraction by extractive distillation using a selective solvent. The process is carried out in a dividing wall column (TK) in which a dividing wall (T) is arranged in the longitudinal direction of the column to form a first subregion (A), a second subregion (B) and a lower joint column region (C) and which is preceded by an extractive scrubbing column (K).

According to WO 2013/083536, a gaseous purified crude $C_4$ fraction is provided as feed stream for an extractive distillation by the liquid crude $C_4$ fraction being fed into the upper third of a distillation column to form an enrichment section and a stripping section, and an overhead stream comprising $C_3$-hydrocarbons and a bottom stream comprising $C_4$ oligomers and $C_4$ polymers and also the $C_{5+}$-hydrocarbons is taken off from the distillation column and the gaseous purified crude $C_4$ fraction is taken off as side stream from the stripping section.

The earlier European patent application 17153120.5 discloses a process for isolating pure 1,3-butadiene from a crude $C_4$ fraction by extractive distillation using a selective solvent. The process employs a predistillation column from which a first low boiler fraction comprising $C_3$-hydrocarbons is taken off as overhead stream, a gaseous $C_4$ fraction is taken off as side stream and a first high boiler fraction is taken off as bottom stream. The predistillation column is divided into an inflow region and a side offtake region by a dividing wall running in the longitudinal direction of the predistillation column. The gaseous $C_4$ fraction is brought into contact with a selective solvent, giving an overhead fraction comprising butanes and butenes and a bottom fraction comprising 1,3-butadiene and selective solvent. Crude 1,3-butadiene is desorbed from the bottom fraction. The crude 1,3-butadiene is freed of a second high boiler fraction in a pure distillation column.

1,3-Butadiene is a polymerizable compound and can form undesirable polymeric deposits, which can, depending on the molecular weight and degree of crosslinking, be rubber-like or brittle (known as popcorn polymers), in various regions of the plant. The rubber-like coatings hinder heat transfer and lead to a reduction in cross sections of conduits. The formation of popcorn polymers can cause severe damage in the interior of the plant and lead to bursting of condensers and conduits. The deposits normally have to be removed from columns and pipes with great effort and loss-producing downtimes.

The construction and operation of a 1,3-butadiene extraction plant comprising predistillation column, extraction and outgassing columns and pure distillation column incur high specific capital and operating costs. In the pure distillation column there is a high safety risk due to formation of popcorn polymers because of the high 1,3-butadiene concentration. It is therefore desirable to simplify the plant and the operation thereof.

The object is achieved by a process for isolating pure 1,3-butadiene from a crude $C_4$ fraction, which produces pure 1,3-butadiene having a prescribed maximum content of at least one low boiler and a prescribed maximum content of 1,2-butadiene, in each case based on 1,3-butadiene, wherein a) a low boiler fraction and a high boiler fraction are separated off by distillation from the crude $C_4$ fraction, giving a purified $C_4$ fraction whose content of the at least one low boiler, based on 1,3-butadiene, is equal to or lower than the prescribed maximum content of the at least one low boiler and whose content of 1,2-butadiene, based on 1,3-butadiene, is equal to or lower than the prescribed maximum content of 1,2-butadiene;

b) the purified $C_4$ fraction is subjected to at least one extractive distillation using a selective solvent, giving at least a fraction comprising butanes and butenes and a pure 1,3-butadiene fraction.

The low boilers, i.e. components which (at the operating pressure of the distillation in step a)) have a boiling point lower than that of 1,3-butadiene, comprised in the crude $C_4$ fraction are removed via the low boiler fraction. Low boilers are, in particular, $C_3$-hydrocarbons such as propane or propyne (methylacetylene). The at least one low boiler is preferably propyne. Propyne is a critical $C_3$ component since any other $C_3$-hydrocarbons such as propane would also be removed in step b) together with the raffinate 1 down to below the detection limit. It is therefore desirable to decrease the content of propyne as early as in the predistillation to a value below the desired specification limit for pure 1,3-butadiene. The prescribed maximum content of propyne is generally 20 ppm, preferably 10 ppm, based on 1,3-butadiene (all ppm figures are ppm by mass).

Since 1,3-butadiene and 1,2-butadiene have similar solubilities in selective solvents, they cannot readily be separated by extractive distillation. According to the invention, the content of 1,2-butadiene in the $C_4$ fraction is therefore reduced to a value below the desired 1,2-butadiene specification limit for pure 1,3-butadiene as early as in a predistillation. 1,2-Butadiene is the high boiler component in the crude $C_4$ fraction which has the smallest boiling point difference compared to 1,3-butadiene. In general, a $C_4$ fraction which meets the 1,2-butadiene specification likewise meets the $C_{5+}$-hydrocarbon specification for 1,3-butadiene.

The prescribed maximum content of 1,2-butadiene is generally 25 ppm, in particular 15 ppm, based on 1,3-butadiene.

The pure 1,3-butadiene often also has a prescribed maximum content of $C_{5+}$-hydrocarbons, based on 1,3-butadiene, and the content of $C_{5+}$-hydrocarbons of the purified $C_4$ fraction is equal to or lower than the prescribed maximum content of $C_{5+}$-hydrocarbons. The prescribed maximum content of $C_{5+}$-hydrocarbons is generally 20 ppm, preferably 10 ppm, based on 1,3-butadiene.

Components which have a boiling point higher than that of 1,3-butadiene and are comprised in the crude $C_4$ fraction are removed via the high boiler fraction. 1,2-Butadiene as key component is removed to a content below the specification limit. $C_{5+}$-Hydrocarbons and the $C_4$ oligomers and $C_4$ polymers comprised in the crude $C_4$ fraction are discharged in their entirety. Carbonyls such as formaldehyde, acetaldehyde, propionaldehyde, n-butyraldehyde, crotonaldehyde, acetone, methyl ethyl ketone or acroleins are also discharged in their entirety via the high boiler fraction. Since no $C_{5+}$ components, in particular very readily polymerizable $C_5$-dienes such as isoprene or cis-2-pentadiene, are conveyed from the predistillation to the extractive distillation, these do not accumulate in the selective solvent.

The low boiler fraction and the high boiler fraction can be separated off by means of a sequence of distillation columns, with the low boiler fraction being separated off at the top from a first column and the bottom product from the first column being distilled in a second column, and the purified $C_4$ fraction being taken off at the top and the bottom product from the second column being taken off as high boiler fraction. It is also possible for high boilers to be separated off first and low boilers to be separated off subsequently.

However, the low boiler fraction and the high boiler fraction are preferably separated off in a dividing wall column or a thermally coupled distillation column. Descriptions of the structure and function of dividing wall columns and thermally coupled columns may be found, for example, in Chem.-Ing. Techn. 61(1989) No. 2, pp. 104-112 and in Gas Separation and Purification, 4(1990) No. 2, pp. 109-114. The dividing wall column or the thermally coupled distillation column allows a feed mixture composed of three or more components to be separated into virtually pure individual components with a low energy consumption. Although equivalent in terms of the energy balance, the dividing wall column has the additional advantage over the thermally coupled column that a single column is used here instead of two separate distillation columns.

The dividing wall column is divided in a middle section into an inflow region and a side offtake region by a dividing wall which runs essentially in the longitudinal direction of the predistillation column. Here, the liquid crude $C_4$ fraction is introduced into the inflow region and the gaseous $C_4$ fraction is taken off from the side offtake region. A low boiler fraction comprising $C_3$-hydrocarbons is taken off as overhead stream, and a high boiler fraction is taken off as bottom stream.

The dividing wall column comprises separation-active internals such as separation trays, structured packings or disordered beds. Separation trays or disordered beds are preferred. Among separation trays, preference is given to using bubble cap trays and valve trays; preferred packing elements for disordered beds are IMTP®, Intalox® Ultra, Raschig® Super Ring, Cascade Mini Ring® or Nutter® Ring. The dividing wall column can, for example, be operated at a temperature at the bottom of from 50 to 100° C. and at a pressure of from 4 to 10 bar. All the pressures indicated in the present document are absolute pressures.

The separating power of a distillation column or a column section is usually reported as the number of theoretical plates present therein. A theoretical plate, in the literature often also referred to as "theoretical separating stage", is the column unit which brings about enrichment in a more volatile component corresponding to the thermodynamic equilibrium between the liquid and vapor in a single distillation event. The dividing wall column has, in particular, from 30 to 100 theoretical plates or particularly preferably from 50 to 80 theoretical plates. The dividing wall generally extends over from 4 to 60, preferably over from 6 to 50, theoretical plates.

In one embodiment, the purified $C_4$ fraction is taken off in gaseous form as side stream from the dividing wall column. The dividing wall column thus simultaneously brings about purification and vaporization of the crude $C_4$ fraction. In other embodiments, the purified $C_4$ fraction taken off in liquid form is vaporized in a separate vaporizer.

The purified $C_4$ fraction is subjected to at least one extractive distillation using a selective solvent, giving at least a fraction comprising butanes and butenes and a pure 1,3-butadiene fraction. The fraction comprising butanes and butenes is usually referred to as raffinate 1. In general, at least one further fraction, i.e. an acetylene fraction comprising the $C_4$-acetylenes ethylacetylene and vinylacetylene, is additionally obtained. The selective solvent which has been freed of acetylenes will also be referred to here as outgassed selective solvent.

The raffinate 1 obtained in the process of the invention is largely free of $C_3$-hydrocarbons, $C_{5+}$-hydrocarbon and carbonyls which can interfere in various ways in downstream plants.

Owing to the high reactivity of 1,3-butadiene, reactive oligomers and polymers of 1,3-butadiene and also 4-vinylcyclohexene (hereinafter vinylcyclohexene), which is a dimerization product of 1,3-butadiene, are inevitably formed during the extraction and the outgassing of the selective solvent. The 1,3-butadiene oligomers and vinylcyclohexene likewise accumulate in the selective solvent because of their higher boiling point compared to $C_4$-hydrocarbons. Even when 1,3-butadiene polymers and oligomers and also vinylcyclohexene are virtually completely removed in the predistillation column, their reformation cannot be completely suppressed. In order to avoid accumulation of vinylcyclohexene in the process, vinylcyclohexene is preferably likewise desorbed or stripped from the selective solvent. Vinylcyclohexene can preferably be removed via the acetylene fraction.

The simplest way of removing 1,3-butadiene oligomers and polymers is to discharge an amount of solvent by means of which an amount of 1,3-butadiene oligomers and polymers corresponding to the amount introduced is removed. However, preference is given to a substream of the selective solvent being, continuously or periodically, subjected to a work-up in which 1,3-butadiene oligomers and polymers are removed, e.g. by distillation. Such a process work-up stage is present in any case in butadiene extraction plants in order to remove various chemicals such as antifoams or inhibitors, polymers, oligomers and decomposition products of the selective solvent from the outgassed solvent.

A loaded solvent fraction comprising 1,3-butadiene and selective solvent is obtained in the extractive distillation. Crude 1,3-butadiene is desorbed from the loaded solvent fraction. Since the outgassed selective solvent comprises a finite concentration of vinylcyclohexene, the crude 1,3-butadiene can have a concentration of vinylcyclohexene which can be above the typical specification limit. It is therefore proposed, in one embodiment, that the crude 1,3-butadiene be scrubbed in a rectification zone with liquid 1,3-butadiene which is obtained by condensation of the vapor obtained at the top of the rectification zone. The vapor obtained at the top of the rectification zone is condensed in a condenser. Part of the condensate can be returned as runback to the rectification zone via a reflux divider, while the other part is discharged as pure 1,3-butadiene. As a result of the reflux, vinylcyclohexene and solvent residues are condensed and the pure 1,3-butadiene obtained at the top of the rectification zone meets the specification criteria.

The rectification zone comprises separation-active internals, preferably separation trays, more preferably sieve trays, bubble cap trays and valve trays. The rectification zone comprises at least 2, preferably at least 4, in particular from 4 to 8, theoretical plates. In one embodiment, the rectification zone comprises from 6 to 10 practical trays.

In general, the pure 1,3-butadiene obtained is not subjected to any further distillation, in particular for removing 1,2-butadiene and/or $C_{5+}$-hydrocarbons (including $C_4$-oligomers and $C_4$-polymers).

The crude 1,3-butadiene, which can still comprise $C_4$-acetylenes, desorbed from the loaded solvent fraction is typically extracted using outgassed selective solvent. For this purpose, the crude 1,3-butadiene is brought into contact with outgassed selective solvent in an after-scrubbing zone. Here, the $C_4$-acetylenes still comprised in the crude 1,3-butadiene are extracted. From the after-scrubbing zone, the crude 1,3-butadiene which has been freed of $C_4$-acetylenes can be fed into the above-described rectification zone.

Step b) can comprise two extractive distillation steps. In a first section, the purified $C_4$ fraction and the selective solvent are fed into a first extractive distillation column in which the purified $C_4$ fraction is fractionated to give two fractions: a raffinate 1 overhead product which comprises the components butanes and butenes which are less soluble in the selective solvent, and the bottom product which comprises the selective solvent together with the butadiene and $C_4$-acetylenes such as vinylacetylene dissolved therein, which represent the more soluble components. The selective solvent together with the butadiene and $C_4$-acetylenes dissolved therein is fed into a first stripper in which the butadienes and $C_4$-acetylenes are stripped from the selective solvent and are conveyed via the top into the second extractive distillation column. The stripped selective solvent is sent back into the first extractive distillation column.

In the second extractive distillation column, the butadiene/acetylene stream from the first section is once again fractionated to give two fractions: a 1,3-butadiene overhead fraction and a bottom fraction which comprises the selective solvent and $C_4$-acetylenes which are more readily soluble than 1,3-butadiene in the selective solvent. The bottom product from the second extractive distillation is treated in a second stripper in which a $C_4$-acetylene-rich product is stripped out of the selective solvent. The same selective solvent or different selective solvents can be used in the first extractive distillation column and in the second extractive distillation column.

In the preferred embodiment, step b) comprises a single-stage extraction with a fractional desorption. Here, the hydrocarbons absorbed in the selective solvent are desorbed in the order which is the reverse of the order of their affinity with the selective solvent.

The gaseous purified $C_4$ fraction is brought into contact with a selective solvent in at least one extraction column, giving an overhead fraction comprising butanes and butenes and a bottom fraction comprising 1,3-butadiene, $C_4$-acetylenes and selective solvent. The gaseous $C_4$ fraction is normally brought into contact with the selective solvent by conveying the gaseous $C_4$ fraction in countercurrent to the selective solvent in at least one section of the extraction column(s).

Instead of using a single extraction column, it can be advantageous for capital cost reasons to couple two columns in such a way that they thermodynamically have the same total number of theoretical plates as the single column. The extraction column and the outgassing column(s) can each also be integrated completely or partly into an integrated extraction and outgassing column. The extraction and outgassing column can be preceded by (a) further extraction column(s) and/or be followed by (a) further outgassing column(s). When a further outgassing column is installed downstream of the integrated extraction and outgassing column, the integrated column will in the present document be referred to as an extraction and preoutgassing column.

The process parameters such as pressure, temperature and solvent ratio are set in the extraction column in such a way that those components of the $C_4$ fraction for which the selective solvent has a lower affinity than for 1,3-butadiene, in particular the butanes and the butenes, remain mainly in the gas phase while 1,3-butadiene and acetylenes and further hydrocarbons for which the selective solvent has a greater affinity than for 1,3-butadiene are virtually completely absorbed by the selective solvent. The overhead fraction comprising butanes and butenes and the bottom fraction comprising 1,3-butadiene, $C_4$-acetylenes and selective solvent are thus obtained. The overhead fraction is usually referred to as raffinate 1. The extraction column can, for example, be operated at a temperature of from 20 to 80° C.

and at a pressure of from 3 to 6 bar. The pressure is advantageously selected so that the overhead condenser of the extraction column can be operated using a readily available coolant such as cooling water.

The bottom fraction comprises not only the solvent and 1,3-butadiene but generally also further hydrocarbons for which the selective solvent has a greater affinity than for 1,3-butadiene, e.g. $C_4$-acetylenes.

In one embodiment, the bottom fraction from the extraction column is conveyed into an extraction and preoutgassing column. The upper part of the extraction and preoutgassing column acts as stripping section in which the butanes and butenes and also other low boilers still dissolved in the solvent can be driven off and taken off at the top. The overhead product from the extraction and preoutgassing column can be fed back into the extraction column. The crude 1,3-butadiene which has been desorbed at the bottom of the extraction and preoutgassing column and comprises small amounts of $C_4$-acetylenes and vinylcyclohexene in addition to 1,3-butadiene can be taken off as side offtake stream from the extraction and preoutgassing column. Preoutgassed solvent, which still comprises various $C_4$ components such as vinylacetylene, is obtained at the bottom of the extraction and preoutgassing column. The extraction and preoutgassing column can, for example, be operated at a temperature at the bottom of from 20 to 80° C. and at a pressure of from 3 to 6 bar.

The preoutgassed solvent obtained at the bottom of the extraction and preoutgassing column is preferably fed into an outgassing column in which further hydrocarbons for which the selective solvent has a greater affinity than for 1,3-butadiene, e.g. $C_4$-acetylenes, are desorbed. Vinylcyclohexene is preferably also desorbed together with $C_4$-acetylenes. The outgassing column can, for example, be operated at a temperature of from 120 to 200° C. and at a pressure of from 1.2 to 6 bar.

The gas comprising $C_4$-acetylenes and vinylcyclohexene is preferably taken off as side offtake stream from the outgassing column. For example, the gas comprising $C_4$-acetylenes which has been taken off as side offtake stream from the outgassing column can be scrubbed with water in an acetylene scrubber in order to recover selective solvent. The acetylene scrubber can be configured as side column of the outgassing column. The scrubbing water can be recycled to the solvent circuit, e.g. into the outgassing column and/or the extraction and preoutgassing column. Water vapor entrained by the scrubbed gas comprising $C_4$-acetylenes can be condensed out and recirculated in its entirety or partly to the acetylene scrubber.

To recover that part of the 1,3-butadiene which is desorbed only in the outgassing column, the overhead product from the outgassing column can be compressed and recirculated into the extraction and preoutgassing column. The overhead product from the outgassing column is appropriately cooled, e.g. by means of a direct cooler, before compression.

As an alternative, the outgassing column is operated at the same pressure level as the extraction and preoutgassing column, so that the overhead product from the outgassing column can be recirculated without increasing the pressure into the extraction and preoutgassing column. Since polymerizable $C_5$-dienes such as isoprene or cis-2-pentadiene are removed as early as in the predistillation in the process of the invention, there is no risk of fouling in the outgassing column.

An outgassed selective solvent is obtained at the bottom of the outgassing column, and this can firstly be used for heat recovery and is, after final cooling, recirculated partly to the extraction column and partly to the after-scrubbing zone described below.

The desorbed crude 1,3-butadiene from the bottom fraction from the extraction and preoutgassing column, which can still comprise various $C_4$ components and vinylcyclohexene, is preferably treated in succession in an after-scrubbing zone with outgassed selective solvent and in a rectification zone with liquid 1,3-butadiene which is obtained by condensation of the vapor obtained at the top of the rectification zone. In the after-scrubbing zone, the crude 1,3-butadiene is brought into contact with outgassed selective solvent. Here, the $C_4$-acetylenes still comprised in the crude 1,3-butadiene are extracted. The solvent running out from the after-scrubbing zone can be conveyed into the extraction and preoutgassing column.

In the rectification zone, the crude 1,3-butadiene which has been freed of acetylenes is scrubbed in a with liquid 1,3-butadiene which has been obtained by condensation of the vapor obtained at the top of the rectification zone. The vapor obtained at the top of the rectification zone is condensed in a condenser. Part of the condensate can be returned as runback to the rectification zone via a reflux divider, while the other part is discharged as pure 1,3-butadiene. As a result of the reflux, vinylcyclohexene and solvent residues are condensed and the pure 1,3-butadiene obtained at the top of the rectification zone meets the specification criteria.

The after-scrubbing zone and the rectification zone can be formed by a separate column. In one suitable embodiment, the after-scrubbing zone and the rectification zone are formed in an upper section of the extraction and preoutgassing column separated off by a dividing wall running essentially in the longitudinal direction of the column. In an upper region of the extraction and preoutgassing column, a dividing wall is then arranged in the longitudinal direction of the column to form an after-scrubbing and rectification zone in the upper section and a lower section which at the bottom adjoins the dividing wall and serves for desorption. The dividing wall is preferably arranged away from the middle so that the cross-sectional area of the after-scrubbing and rectification zone is smaller than the cross-sectional area of the extraction zone.

The water content of the pure 1,3-butadiene condensed at the top of the rectification zone corresponds to the physical solubility of water in 1,3-butadiene. In most cases, lower water contents are desired or prescribed. In these cases, the pure 1,3-butadiene can be subjected to removal of water in a further step.

To remove water, the pure 1,3-butadiene can, for example, be cooled; this reduces the physical solubility of water in 1,3-butadiene and the now no longer completely soluble water forms a separate phase which can be separated off. As an alternative, water can be removed in a stripping column. In the stripping column, the pure 1,3-butadiene is stripped by means of a stripping vapor which is obtained by partial vaporization of the pure 1,3-butadiene at the bottom of the stripping column. The vapor obtained at the top of the stripping column is condensed and the condensate is subjected to phase separation into an aqueous phase and an organic phase. The organic phase can be conveyed as runback into the stripping column. Dewatered pure 1,3-butadiene is taken off at the bottom. Other methods of dewatering the pure 1,3-butadiene, e.g. reverse osmosis or adsorption, are likewise conceivable.

The part of the vapor which has not been condensed at the top of the rectification zone is taken off as outlet stream. The outlet stream consists essentially of 1,3-butadiene with traces of water vapor, oxygen and inert gases. The outlet stream serves to discharge oxygen and inert gases. In this way, the oxygen content in the extraction and preoutgassing column can be brought to below the detection limit of conventional oxygen detectors. The presence of small amounts of molecular oxygen in the lower ppm range or below has been recognized as a main cause of the undesirable formation of butadiene polymers in the columns and plant components.

In a preferred embodiment of the process of the invention, the outlet stream from the rectification zone is conveyed together with the vapor from the predistillation column through the overhead condenser of the predistillation column. The outlet stream from the rectification zone can, for example, be introduced at the top of the predistillation column or into the feed conduit to the condenser. 1,3-Butadiene comprised in the outlet stream from the rectification zone is not lost in this way of carrying out the process. The overhead condenser of the predistillation column is operated in such a way that $C_3$-hydrocarbons are separated off as overhead stream while higher hydrocarbons are condensed and returned as runback to the predistillation column. The 1,3-butadiene therefore condenses virtually completely in terms of the mass balance in the overhead condenser of the predistillation column, flows into the predistillation column and forms part of the gaseous $C_4$ fraction taken off therefrom as side stream.

In a further preferred embodiment, a gaseous outlet stream from the extraction column is also provided. The outlet is preferably arranged at or downstream of the condenser, e.g. at the distillate collector, i.e. the remaining gas constituents which are not condensed in the overhead condenser of the extraction column are discharged. These uncondensed constituents consist essentially of butanes, butenes, inert gases such as nitrogen and subordinate amounts of molecular oxygen. The outlet stream from the extraction column can advantageously be used to dilute the $C_4$-acetylene-comprising gas which is desorbed in the outgassing column.

The crude $C_4$ fraction comprises at least 1,3-butadiene and butenes. In most cases, the crude $C_4$ fraction comprises 1,3-butadiene, butanes, butenes and $C_4$-acetylenes. In many cases, the crude $C_4$ fraction comprises 1,3-butadiene, 1,2-butadiene, butanes, butenes and $C_4$-acetylenes, $C_3$-hydrocarbons and $C_{5+}$-hydrocarbons. For the present purposes, $C_{5+}$-hydrocarbons are hydrocarbons having five or more carbon atoms.

The crude $C_4$ fraction is, for example, a crude $C_4$ fraction from a naphtha cracker.

A typical crude $C_4$ fraction from a naphtha cracker has the following composition in percent by weight:

| | |
|---|---|
| propane | 0-0.5 |
| propene | 0-0.5 |
| propadiene | 0-0.5 |
| propyne | 0-0.5 |
| n-butane | 3-10 |
| i-butane | 1-3 |
| 1-butene | 10-20 |
| i-butene | 10-30 |
| trans-2-butene | 2-8 |
| cis-2-butene | 2-6 |
| 1,3-butadiene | 15-85 |
| 1,2-butadiene | 0.1-1 |
| ethylacetylene | 0.1-2 |
| vinylacetylene | 0.1-3 |
| $C_5$-hydrocarbons | 0-0.5 |

Crude $C_4$ fractions from naphtha crackers thus comprise predominantly butanes, butenes and 1,3-butadiene. In addition, small amounts of other hydrocarbons are comprised. $C_4$-Acetylenes are occasionally comprised in a proportion of up to 5% by weight and frequently up to 2% by weight.

Possible selective solvents are substances or mixtures in general which have a boiling point higher than that of the mixture to be fractionated and also a greater affinity for conjugated double bonds and triple bonds than for isolating double bonds and single bonds, preferably dipolar solvents, particularly preferably dipolar aprotic solvents. For reasons of protecting the apparatus, substances which have little corrosivity or are not corrosive are preferred. Suitable selective solvents for the process of the invention are, for example, nitriles such as acetonitrile, propionitrile, methoxypropionitrile, ketones such as acetone, furfuryl alcohol, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, in particular N-methylpyrrolidone (NMP). Use is generally made of N-alkyl-substituted lower aliphatic acid amides or N-alkyl-substituted cyclic acid amides. Dimethylformamide, acetonitrile, furfuryl alcohol and in particular N-methylpyrrolidone are particularly advantageous.

However, it is also possible to use mixtures of these solvents with one another, for example of N-methylpyrrolidone with acetonitrile, and mixtures of these solvents with cosolvents such as water, and alcohols, in particular those having 5 or fewer carbon atoms, e.g. methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, or alicyclic alcohols such as cyclopentanol, diols such as ethylene glycol and/or tert-butyl ethers, for example methyl tert-butyl ether, ethyl tert-butyl ether, propyl tert-butyl ether, n-butyl or isobutyl tert-butyl ether.

In one preferred embodiment of the process of the invention, the selective solvent comprises at least 80% by weight of N-methylpyrrolidone. The selective solvent preferably comprises from 85 to 95% by weight of NMP and from 5 to 15% by weight of water. N-methylpyrrolidone is particularly useful, preferably in aqueous solution, in particular with from 7 to 9% by weight of water, particularly preferably with 8.3% by weight of water.

In addition, the selective solvent can, in particular, further comprise auxiliaries such as inhibitors or antifoams. Organic secondary components can be comprised as impurity.

The invention is illustrated by the attached drawing and the following examples.

FIG. 1 schematically shows a preferred plant for carrying out the process of the invention.

A liquid crude $C_4$ fraction 1 is introduced into the predistillation column K1. The predistillation column K1 is divided in a middle section by a dividing wall 2 running essentially in the longitudinal direction of the predistillation column K1 into an inflow region 3 and a side offtake region 4. The inflow region 3 and the side offtake region 4 each extend in the vertical direction from the upper end to the lower end of the dividing wall 2. A gaseous $C_4$ fraction 7 is taken off from the side offtake region 4. The vapor from the predistillation column K1 is conveyed through the overhead condenser 5. The condensate formed therein is returned to the predistillation column K1. The uncondensed part of the vapor forms the overhead stream 6 which is taken off as a low boiler fraction from the predistillation column K1. In addition, a high boiler fraction is taken off as bottom stream 9 from the predistillation column K1. The bottom of the predistillation column K1 is heated by means of the vaporizer 8.

The gaseous $C_4$ fraction 7 is fed into a lower section of an extraction column K2 and in this column is brought into contact with an outgassed selective solvent 10 which is fed into an upper section of the extraction column K2. Condensation of the vapor from the extraction column K2 in the condenser 11 gives an overhead fraction 12 (known as raffinate I) comprising butanes and butenes and also an uncondensed part 13 of the vapor. The stream 13 serves as diluent gas for the acetylenes 32. At the same time, the stream 13 is outlet stream for the extraction column K2 in order to control the content of molecular oxygen in the gas space of the extraction column K2. In addition, a bottom fraction 14 which consists essentially of selective solvent in which not only 1,3-butadiene but also vinylacetylene, ethylacetylene and vinylcyclohexene and also butanes and butenes are dissolved is obtained.

The bottom fraction 14 is introduced into an upper section 15 of an extraction and preoutgassing column K3. An after-scrubbing zone 16A and a rectification zone 16B are separated off from the upper section of the extraction and preoutgassing column K3 by a dividing wall running essentially in the longitudinal direction of the column. A substantial part of the crude 1,3-butadiene is desorbed in the lower section 18 of the extraction and preoutgassing column K3. In the after-scrubbing zone 16A, the crude 1,3-butadiene is brought into contact with outgassed selective solvent fed in via the side inlet 23 in order to separate off $C_4$-acetylenes. The rectification zone 16B is arranged above the after-scrubbing zone 16A. The rectification zone 16B comprises a number of theoretical plates. Condensation of the vapor 19 in the condenser 20 gives liquid pure 1,3-butadiene 21 and an uncondensed part 38 of the rectification vapor. Part of the condensate 21 of the 1,3-butadiene is recirculated as runback into the rectification zone. In this, the 1,3-butadiene is brought into contact with backflowing condensate in order to separate off high boilers such as vinylcyclohexene and residues of the selective solvent. The other part 22 of the 1,3-butadiene condensate is fed as pure 1,3-butadiene to the optional water removal K5. The bottom of the extraction and preoutgassing column K3 is heated by means of the vaporizer 25. The uncondensed part 38 of the rectification vapor is fed back into the overhead condenser 5 of the predistillation column K1.

A gas 17 which comprises butanes and butenes and is discharged from section 15 at the top of the extraction and preoutgassing column K3 is recirculated into a lower section of the extraction column K2. Thermodynamically, the section 15 of the extraction and preoutgassing column K3 and the extraction column K2 together correspond to a single extraction column which for reasons of the column height has been divided in two vertically.

Preoutgassed solvent from the bottom of the extraction and preoutgassing column K3 is conveyed further as stream 26 into an outgassing column K4. Further crude 1,3-butadiene desorbs in the outgassing column K4 and this is fed into the lower section of the extraction and preoutgassing column K3. In the embodiment shown, the crude 1,3-butadiene desorbed in the outgassing column K4 is conveyed via conduit 27, the optional arrangement of direct cooler K6 and compressor 31 and conduit 24 into the lower section of the extraction and preoutgassing column K3. Cooling medium is introduced and discharged via the conduits 29 and 30. Condensate from the plant, which consists essentially of components of the selective solvent, e.g. water and NMP, serves as cooling medium. The bottom of the outgassing column K4 is heated by means of vaporizer 37.

A gas 28 comprising $C_4$-acetylenes and vinylcyclohexene and also 1,3-butadiene and components of the selective solvent, e.g. water and NMP, is taken off as side offtake stream from the outgassing column K4. The gas 28 comprising $C_4$-acetylenes and vinylcyclohexene is scrubbed with water which is supplied via conduit 36 in the acetylene scrubber K7. The stream 32 obtained at the top of the acetylene scrubber K7 is diluted with the outlet stream 13 from the extraction column K2. Condensable constituents (mainly water and small amounts of vinylcyclohexene) are condensed in the condenser 33 and can be returned as runback 35 to the acetylene scrubber K7; the discharge from the acetylene scrubber K7 is mainly processed wastewater which can be subjected to a phase separation and disposed of. Uncondensed constituents are discharged as stream 34 (dilute acetylene stream).

In the optional water removal K5, which is, for example, configured as a stripping column, a water phase is separated off from the 1,3-butadiene 21.

Example 1

The process of the invention was simulated on the basis of a plant as shown in FIG. 1. The BASF in-house software Chemasim was used for the simulation calculation; comparable results were obtained using commercially available software such as Aspen Plus (manufacturer: AspenTech, Burlington/Mass., USA) or PRO II (Fullerton, USA). The set of parameters was based on comprehensive equilibrium measurements, studies on laboratory columns and operating data from various plants. The target specification for the pure 1,3-butadiene was: at least 99.5% of 1,3-butadiene, not more than 20 ppm of 1,2-butadiene, not more than 20 ppm of acetylenes.

The calculation was carried out assuming a crude $C_4$ fraction comprising 1300 ppm of $C_3$-hydrocarbons, 2.0% of n-butane, 0.6% of isobutane, 19.0% of n-butene, 28.3% of isobutene, 5.5% of trans-2-butene, 4.4% of cis-2-butene, 39.0% of 1,3-butadiene, 0.2% of 1,2-butadiene, 1200 ppm of 1-butyne, 4500 ppm of vinylacetylene and in each case 3000 ppm of $C_5$-hydrocarbons.

The mass flows and compositions of relevant streams are summarized in table 1. The designations of the streams in the table relate to the designations in FIG. 1.

TABLE 1

| | Stream | | | |
|---|---|---|---|---|
| Example 1 | 1 | 7 | 9 | 22 |
| Mass stream [kg/h] | 32 000 | 31 585 | 664 | 12 667 |
| 1,2-Butadiene [% by weight] | 0.15 | 0.0012 | 7.17 | 0.0019 |
| Acetylenes [% by weight] | 0.57 | 0.57 | 0.43 | 0.02 |
| $C_{5+}$ components [% by weight] | 0.30 | 0.002 | 14.45 | |
| 1,3-Butadiene [% by weight] | 39.0 | 40.2 | 1.51 | 99.53 |

A loss of 1,3-butadiene of about 7 kg/h occurs via the single high boiler outlet stream 9. Both the content of $C_5$ components and the content of 1,2-butadiene as the high boilers which are most difficult to separate off are reduced by about 99% in the predistillation column.

Comparative Example

A process according to the prior art was simulated. The composition of the crude $C_4$ fraction and the target specification for the pure 1,3-butadiene corresponded to those in example 1. The plant used as a basis had an upstream distillation column as per WO 2013/083536 A1 into which the liquid crude $C_4$ fraction was fed instead of the predistillation column K1 provided with the dividing wall 2. In addition, the plant of the comparative example had a pure distillation column.

The mass flows and compositions of relevant streams are summarized in table 2.

TABLE 2

| | Stream | | | |
|---|---|---|---|---|
| Comparative example 2 | Crude $C_4$, liquid[1] | Crude $C_4$, purified[2] | Bottom stream from dist.[3] | Bottom stream from pure dist.[4] |
| Mass stream [kg/h] | 32 000 | 31 743 | 110 | 69 |
| 1,2-Butadiene [% by weight] | 0.15 | 0.14 | 40.00 | 40.00 |
| Acetylene [% by weight] | 0.57 | 0.57 | 0.21 | 0.18 |
| $C_{5+}$ Components [% by weight] | 0.30 | 0.13 | 8.38 | 30.18 |
| 1,3-Butadiene [% by weight] | | | 29.88 | 14.88 |

[1] liquid crude $C_4$ fraction (reference symbol 1 in FIG. 1 of WO 2013/083536 A1)
[2] gaseous purified crude $C_4$ fraction (reference symbol 4 in FIG. 1 of WO 2013/083536 A1)
[3] bottom stream obtained from the upstream distillation column (reference symbol 3 in FIG. 1 of WO 2013/083536 A1)
[4] bottom stream obtained in the pure distillation In this process, two $C_{5+}$-comprising high boiler streams, which are discarded, are obtained: the bottom stream from the upstream distillation column and the bottom stream obtained from the pure distillation. There is a loss of 1,3-butadiene of about 43 kg/h. In the upstream distillation column of comparative example 2, only a relatively small proportion of the $C_{5+}$ components were separated off (55%), The $C_{5+}$ components were carried in a far higher proportion into the extraction column via the gaseous purified crude $C_4$ fraction. In addition, a smaller proportion of 1,2-butadiene (75%) was separated off in the upstream distillation column of comparative example 2. As a result, a further removal of 1,2-butadiene in a pure column is necessary in the comparative example in order to obtain a specification of 20 ppm of 1,2-butadiene. This additional subsequent separation is no longer necessary when using the process of the invention.

The invention claimed is:

1. A process for isolating pure 1,3-butadiene from a crude $C_4$ fraction, the process comprising:
    introducing the crude $C_4$ fraction into a predistillation column comprising a dividing wall running in a longitudinal direction of the predistillation column, and taking off a $C_3$ low boiler fraction, comprising $C_3$ hydrocarbons, as an overhead stream from the predistillation column, taking off a high boiler fraction as a bottom stream from the predistillation column, and taking off a purified $C_4$ fraction as a side stream from the predistillation column;
    extractively distilling the purified $C_4$ fraction using a selective solvent to obtain a fraction comprising butanes and butenes and a pure 1,3-butadiene fraction comprising at least 99.5 wt. % 1,3-butadiene,
    wherein the purified $C_4$ fraction comprises a lower boiler in an amount equal to or lower than a prescribed maximum lower boiler content and 1,2-butadiene in an amount equal to or lower than a prescribed maximum 1,2-butadiene content, and
    wherein the prescribed maximum 1,2-butadiene content is 25 ppm, based on 1,3-butadiene.

2. The process of claim 1, wherein the low boiler is propyne.

3. The process of claim 2, wherein the prescribed maximum content of propyne is 20 ppm, based on 1,3-butadiene.

4. The process of claim 3, wherein the prescribed maximum 1,2-butadiene content is 15 ppm, based on 1,3-butadiene.

5. The process of claim 1, wherein the extractively distilling comprises:
    obtaining a loaded solvent fraction comprising 1,3-butadiene and the selective solvent, and desorbing crude 1,3-butadiene from the loaded solvent fraction, and
    scrubbing the crude 1,3-butadiene in a rectification zone comprising at least two theoretical plates with liquid 1,3-butadiene obtained by condensation of a vapor obtained at a top of the rectification zone, giving the pure 1,3-butadiene fraction.

6. The process of claim 5, wherein an acetylene fraction is also desorbed from the loaded solvent fraction, giving an outgassed selective solvent.

7. The process of claim 6, wherein the crude 1,3-butadiene is extracted with the outclassed selective solvent before the scrubbing with the liquid 1,3-butadiene.

8. The process of claim 7, wherein the extractively distilling comprises:
    contacting the purified $C_4$ fraction with the selective solvent in at least one extraction column, giving an overhead fraction comprising butanes and butenes and a bottom fraction comprising 1,3-butadiene and the selective solvent;
    desorbing the crude 1,3-butadiene from the bottom fraction, giving a preoutgassed selective solvent;
    desorbing acetylenes from the preoutgassed selective solvent, giving the outgassed selective solvent;
    extracting the crude 1,3-butadiene with the outgassed selective solvent in an after-scrubbing zone; and
    scrubbing the extracted crude 1,3-butadiene with the liquid 1,3-butadiene in the rectification zone, giving the pure 1,3-butadiene fraction.

9. The process of claim 8, wherein the rectification zone is arranged above the after-scrubbing zone in a column or a column section.

10. The process of claim 8, wherein the purified $C_4$ fraction is brought into contact with the selective solvent in an extraction column and in an upper section of an extraction and preoutgassing column and the crude 1,3-butadiene is desorbed from the bottom fraction in a lower section of the extraction and preoutgassing column and an outgassing column.

11. The process of claim 10, wherein the after-scrubbing zone and the rectification zone are formed in an upper section of the extraction and preoutgassing column which is separated by a dividing wall running in a longitudinal direction of the column.

12. The process of claim 10, wherein an outgassing column is operated at the same pressure level as the extraction and preoutgassing column and an overhead product from the outgassing column is recirculated without increasing pressure into the extraction and preoutgassing column.

13. The process of claim 8, wherein a part of the vapor which has not been condensed at the top of the rectification zone is conveyed together with the vapor from the predistillation column through an overhead condenser of the predistillation column.

14. The process of claim 1, further comprising:
separating off dissolved water from the pure 1,3-butadiene fraction.

15. The process of claim 14, wherein the separating off of the water comprises cooling and phase separating and/or stripping in a stripping column.

16. The process of claim 1, wherein the selective solvent comprises at least 80% by weight of N-methylpyrrolidone.

17. The process of claim 1, wherein the love boiler comprises propyne.

18. The process of claim 1, wherein the selective solvent comprises acetonitrile, propionitrile, methoxypropionitrile, acetone, furfuryl alcohol, dimethylformamide, diethylformamide, dimethylacetamide, diethylacetamide, N-formylmorpholine, and/or N-methylpyrrolidone.

19. The process of claim 1, wherein the selective solvent comprises dimethylformamide, acetonitrile, or furfuryl alcohol.

* * * * *